United States Patent [19]

Lesher et al.

[11] 4,086,233
[45] Apr. 25, 1978

[54] 4-(SUBSTITUTED-AMINO)-2-(PYRIDINYL) PYRIMIDINE DERIVATIVES

[75] Inventors: George Y. Lesher, Schodack; Baldev Singh, East Greenbush, both of N.Y.

[73] Assignee: Sterling Drug Inc., New York, N.Y.

[21] Appl. No.: 765,234

[22] Filed: Feb. 3, 1977

Related U.S. Application Data

[62] Division of Ser. No. 708,195, Jul. 23, 1976, Pat. No. 4,032,523.

[51] Int. Cl.² ............................................. C07D 239/42
[52] U.S. Cl. ....................... 260/256.4 C; 260/256.4 N
[58] Field of Search ................... 260/256.4 C, 256.4 N

[56] References Cited

U.S. PATENT DOCUMENTS

| | | | |
|---|---|---|---|
| 3,673,184 | 6/1972 | Minami et al. | 260/256.4 N |
| 3,931,180 | 1/1976 | Mühle et al. | 260/256.4 C |

*Primary Examiner*—Paul M. Coughlan, Jr.
*Attorney, Agent, or Firm*—Robert K. Bair; B. Woodrow Wyatt

[57] ABSTRACT

Compounds useful as anti-allergic agents are 2-Q-4-[XZC=C(R)NH]-5-$R_1$-6-$R_2$-pyrimidines (I), where Q is 4- or 3- or 2-pyridinyl or 4- or 3- or 2-pyridinyl having one or two lower-alkyl substituents or N-oxide thereof, R is hydrogen or lower-alkyl, $R_1$ is hydrogen, lower-alkyl or cyano, $R_2$ is hydrogen, lower-alkyl, hydroxy or halo, X and Z are the same or different and are each selected from lower-carbalkoxy, lower-alkanoyl, carbamyl and cyano, or

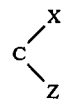

is

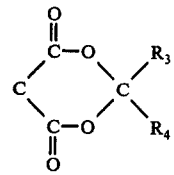

wherein $R_3$ and $R_4$ are each lower-alkyl, or X is hydrogen, are prepared by reacting 4-amino-2-Q-5-$R_1$-6-$R_2$-pyrimidine (II where Q' is amino) with R'O-C(R)=CXZ (III). Preparations of II are given. Also shown as intermediates and/or anti-allergic agents are 4-(AcNH)-2-Q-5-$R_1$-6-$R_2$-pyrimidines (IV) and 4-($R_5R_6$N)-2-Q-5-$R_1$-6-$R_2$-pyrimidines (V) where Ac is lower-alkanoyl or lower-carbalkoxy, $R_5$ is hydrogen, lower-alkyl or lower-hydroxyalkyl, and $R_6$ is lower-alkyl or lower-hydroxyalkyl.

1 Claim, No Drawings

4-(SUBSTITUTED-AMINO)-2-(PYRIDINYL) PYRIMIDINE DERIVATIVES

CROSS-REFERENCE TO RELATED APPLICATIONS

Certain of the di-(lower-alkyl) N-(2-Q-6-R$_2$-4-pyrimidinyl)aminomethylenemalonates (I where R and R$_1$ are each hydrogen and X and Y are each lower-carbalkoxy) disclosed and claimed in copending application Ser. No. 555,067, filed Mar. 3, 1975, now U.S. Pat. No. 4,018,770, issued Apr. 19, 1977, are disclosed as intermediates in the preparation of antibacterially active 5,8-dihydro-5-oxopyrido[2,3-d]pyrimidines which are disclosed and claimed in U.S. patent application Ser. No. 555,051, filed Mar. 3, 1975, now U.S. Pat. No. 3,992,380 issued Nov. 16, 1976.

This application is a division of copending application Ser. No. 708,195, filed July 23, 1976, now U.S. Pat. No. 4,032,523, issued June 28, 1977, which in turn is a division of said copending application Ser. No. 555,067, filed Mar. 3, 1975.

BACKGROUND OF THE INVENTION a. Field of the Invention

This invention relates to pyrimidinylaminomethylenemalonate derivatives and analogs which are useful as anti-allergic agents, and to intermediates and processes for their preparation.

b. Description of the Prior Art

The Sterling Drug Inc. Lesher U.S. Pat. No. 3,320,257, issued May 16, 1967, discloses, inter alia, dialkyl N-(2-R$_2$-6-R$_4$-4-pyrimidinyl)aminomethylenemalonates where R$_2$ and R$_4$ are each hydrogen, lower-alkyl, lower-alkoxy, lower-alkylamino, lower-alkylmercapto, phenylmethyl, phenyloxy, phenylamino or phenylmercapto. The compounds are shown to be useful as intermediates for preparing anti-bacterially active 5,8-dihydro-8-(lower-alkyl)-2-R$_2$-5-oxopyrido[2,3-d]pyrimidine-6-carboxylic acids.

The Dainippon Pharmaceutical Co., Ltd. British Patent Specification No. 1,129,358, published Oct. 2, 1968, discloses as intermediates for preparing antibacterially active 5,8-dihydro-5-oxopyrido[2,3-d]pyrimidines certain N-[2-R$_3$-6-R$_2$-4-pyrimidinyl]aminomethylenemalonates where R$_2$ is hydrogen, a lower alkyl radical, a hydroxy group, a halogen atom, a lower alkoxy radical, an amino group or a lower alkylthio radical and R$_3$ is hydrogen, a lower alkyl radical, a hydroxy group, a lower alkoxy radical, a lower alkylthio group or a radical of formula

(in which R' is hydrogen, an alkyl radical, a cycloalkyl radical, an amino group, a hydroxyalkyl radical or an alkyl-substituted aminoalkyl radical, R'' is hydrogen or an alkyl radical or R' and R'', together with the nitrogen atom to which they are bonded, form a heterocyclic ring).

SUMMARY OF THE INVENTION

In one composition aspect, the invention relates to certain N-[2-(pyridinyl)-5-R$_1$-6-R$_2$-4-pyrimidinyl]-aminomethylenemalonates and analogs (I), which are useful as anti-allergic agents.

In another composition aspect, the invention relates to 2-Q-4-Q'-5-R$_1$-6-R$_2$-pyrimidines (II) which are useful as intermediates in the preparation of the above final products (I), and some of which are useful as anti-allergic agents.

The invention in a process aspect comprises reacting a compound of formula II where Q' is amino with a compound of the formula R'O-C(R)=CXZ to produce the compound of formula I.

In another composition aspect, the invention relates to 2-Q-4-AcNH-5-R$_1$-6-R$_2$-pyrimidines (IV) which are useful as intermediates and some as anti-allergic agents.

In another composition aspect, the invention relates to 2-Q-4-R$_5$R$_6$N-5-R$_1$-6-R$_2$-pyrimidines (V) which are useful as anti-allergic agents.

DETAILED DESCRIPTION INCLUSIVE OF PREFERRED EMBODIMENTS

The invention in a composition aspect resides in the compounds having formula I

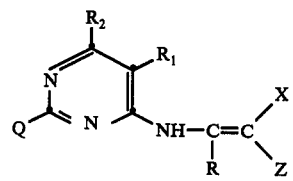

where Q is 4- or 3- or 2-pyridinyl or 4- or 3- or 2-pyridinyl having one or two lower-alkyl substituents of N-oxide thereof, R is hydrogen or lower-alkyl, R$_1$ is hydrogen, lower-alkyl or cyano, R$_2$ is hydrogen, lower-alkyl, hydroxy or halo, X and Z are the same or different and are each selected from lower-carbalkoxy, lower-alkanoyl, carbamyl and cyano or

is

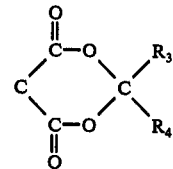

where R$_3$ and R$_4$ are each lower-alkyl, or X is hydrogen. The compounds of formula I are useful as anti-allergic agents, as determined by standard pharmacological evaluation procedures. Preferred embodiments are those having formula I where R, R$_1$ and R$_2$ are each hydrogen, X and Z are each lower-carbalkoxy and Q is 4(or 3)-pyridinyl, particularly preferred embodiments being those where X and Z are each carbomethoxy (COOCH$_3$) or carbethoxy (COOC$_2$H$_5$). The compounds of formula I where Q is 4(or 3)-pyridinyl or 4(or 3)-pyridinyl having one or two lower-alkyl substituents, R$_2$ is hydrogen or lower-alkyl, R and R$_1$ are each hydrogen, and X and Z are each lower-carbalkoxy are disclosed as intermediates for preparing lower-alkyl 5,8- dihydro-5-oxo-2-Q-4-$R_2$-pyrido[2,3-d]pyrimidine-6-carboxylates and corresponding 1-(lower-alkyl)-6-carboxylic acids in application Ser. No. 555,051, filed Mar. 3, 1975, now U.S. Pat. No. 3,992,380, issued Nov. 16, 1976.

The invention in another composition aspect resides in the compounds having formula II

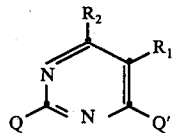

II where Q, $R_1$ and $R_2$ have the meanings given above for formula I and Q' is hydroxy, halo, hydrazino ($NHNH_2$) or amino ($NH_2$). These compounds are useful in the preparation of the compounds of formula I and other than the compounds where Q' is halo also are useful as anti-allergic agents. The compounds of formula II are disclosed and claimed in said U.S. Pat. No. 4,032,523.

The invention in a process aspect comprises reacting a compound of formula II where Q' is amino with a compound of the formula III

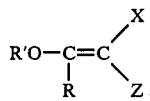

III to produce the compound of formula I, where R' is lower-alkyl, and R, X and Z each is defined as given above for formula I and, optionally, reacting I where Q represents other than a pyridinyl N-oxide with an oxidizing agent capable of converting pyridines to pyridine-N-oxides to produce the corresponding compounds (I) where Q is a pyridinyl N-oxide.

The invention in another composition aspect resides in the compounds having formula IV

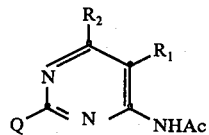

IV where Q, $R_1$ and $R_2$ have the meanings given above for formula I and Ac is lower-alkanoyl or lower-carbalkoxy. These compounds, as shown hereinbelow, are useful as intermediates in the preparation of the compounds of formula II where Q' is amino and Q is a pyridinyl N-oxide. Also, compounds of formula IV where Ac is lower-carbalkoxy are useful as anti-allergic agents.

The invention in another composition aspect resides in the compounds having formula V

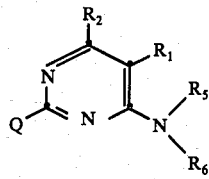

V where Q, $R_1$ and $R_2$ have the meanings given above for formula I, $R_5$ is hydrogen, lower-alkyl or lower-hydroxyalkyl and $R_6$ is lower-alkyl or lower-hydroxyalkyl, which are useful as anti-allergic agents.

The term "lower-alkyl" as used herein, e.g., as one of the meanings for R, $R_1$ or $R_2$ or as a substituent for Q in formulas I, II, III, IV or V, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The term "lower-carbalkoxy", as used herein, e.g., as one of the meanings for X or Z in formula I or III or as one of the meanings for Ac in formula IV, means carbalkoxy radicals where the alkoxy portion can be straight- or branch-chained and has from one to six carbon atoms, as illustrated by carbomethoxy, carbethoxy, carbo-n-propoxy, carbisopropoxy, carbo-n-butoxy, carbo-tert.-butoxy and carbo-n-hexoxy.

Illustrative of the Q substituent in formulas I or II where Q is 4(3 or 2)-pyridinyl having one or two lower-alkyl substituents are the following [note that "pyridinyl" as used herein is the same as "pyridyl", the former now being the preferred term used in Chemical Abstracts]: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl) 4-methyl-2-pyridinyl, 6-methyl-2-pyridinyl, 2,3-dimethyl-4-pyridinyl, 2,5-dimethyl-4-pyridinyl, 4,6-dimethyl-2-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-di-isopropyl-4-pyridinyl, 2,6-di-n-hexyl-4-pyridinyl, and the like.

The term "lower-alkanoyl", as used herein, e.g., as one of the meanings for X and Z in formulas I and III and as one of the meanings for Ac in formula IV, means alkanoyl radicals having from two to six carbon atoms, including the straight- and branch-chained radicals, illustrated by acetyl, propionyl (n-propanoyl), butyryl (n-butanoyl), isobutyryl (2-methyl-n-propanoyl) and caproyl (n-hexanoyl).

The term "lower-hydroxyalkyl", as used herein, e.g., as one of the meanings for $R_5$ and $R_6$ in formula V, means hydroxyalkyl radicals having from two to six carbon atoms and having its hydroxy group and its free valence bond (or connecting linkage) on different carbon atoms, illustrated by 2-hydroxyethyl, 2-hydroxypropyl, 3-hydroxypropyl, 2-hydroxy-2-methylpropyl, 3-hydroxypropyl, 4-hydroxybutyl, 5-hydroxyamyl, 6-hydroxyhexyl, 2-hydroxy-1,1-dimethylethyl, and the like.

Also, the compounds of formula I and formula II where Q' is amino or hydrazino are useful both in the free base form and in the form of acid-addition salts; and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, medicinally acceptable salts, that is, salts whose anions are relatively innocuous to the animal organism in medicinal doses of the salts, so that the beneficial anti-allergic properties inherent in the free base are not vitiated by side effects ascribable to the anions. In practicing the invention, it was found convenient to form the hydrochloride, methanesulfonate or cyclohexylsulfamate salts. However, other appropriate medicinally acceptable salts within the scope of the invention are those derived from mineral acids such as phosphoric acid, sulfamic acid, and sulfuric acid; and organic acids such as acetic acid, citric acid, tartaric acid, lactic acid, ethanesulfonic acid, benzenesulfonic acid, p-toluenesulfonic acid, quinic acid, and the like, giving the phosphate, sulfamate, acetate, citrate, tartrate, lactate, ethanesulfonate, benzenesulfonate, p-toluenesulfonate and quinate, respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution.

Although medicinally acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

The molecular structures of the composition aspects (I and II) of the invention were assigned on the basis of evidence provided by infrared, ultraviolet, nuclear magnetic resonance and mass spectra, by chromatographic mobilities, and, by the correspondence of calculated and found values for the elementary analyses for representative examples.

The manner of making and using the instant invention will now be generally described so as to enable a person skilled in the art of chemistry to make and use the same, as follows:

The preparation of the compounds of formula I is carried out by reacting a 4-amino-2-Q-5-$R_1$-6-$R_2$-pyrimidine (formula II where Q' is amino) where Q, $R_1$ and $R_2$ have the meanings given above for formula I, with a compound of formula III, i.e., R'O-C(R)=CXZ, where R', R, X and Z have the meanings given for formula III. This reaction is carried out by heating said reactants, preferably in a molar ratio of 1:1 and preferably with stirring, either in the absence or presence of a suitable inert solvent, at about 100° C. to 200° C., preferably about 120° C. to 160° C. The reaction is conveniently run by heating the reactants, either in refluxing xylene or in the absence of a solvent at the said preferred heating temperature. Other suitable solvents inert under the reaction conditions include toluene, anisole, nitrobenzene, chlorobenzene, dimethylformamide, dimethylacetamide, tetramethylurea, pyridine, α-picoline, β-picoline, γ-picoline, and the like. Alternatively, the above reaction can be carried out by preparing the reactant of formula III

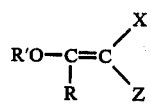

in situ without its actual isolation by heating a mixture of equimolar quantities of the compound of formula II where Q' is amino, tri-(lower-alkyl) orthoformate, preferably the triethyl ester, and a compound of formula VI

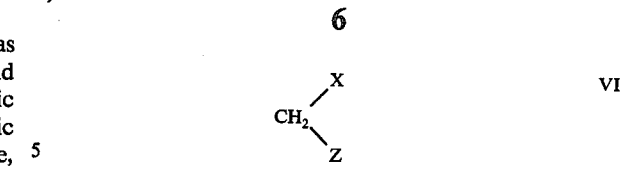

where X and Z have the meanings given for formulas I and III, under the reaction conditions discussed above. Preferably, the reaction is run in the presence of a catalytic amount of an acidic catalyst, e.g., a strong inorganic acid such as hydrochloric acid, sulfuric acid, hydrobromic acid, phosphoric acid, and the like; an organic sulfonic acid such as p-toluenesulfonic acid, benzenesulfonic acid, methanesulfonic acid, ethanesulfonic acid, and the like; a Lewis acid such as zinc chloride, boron trichloride, boron tribromide, aluminum trichloride; other strong organic acid, e.g., trifluoroacetic acid, and the like.

The reaction of the compound of formula I where Q is other than a pyridinyl N-oxide with an oxidizing agent to produce the compound of formula I where Q is a pyridinyl N-oxide is carried out by reacting compound of formula I where Q is other than a pyridinyl N-oxide with an oxidizing agent capable of converting pyridines to pyridine N-oxides, preferably with a per acid, e.g., peracetic acid, perbenzoic acid, 3-chloroperbenzoic acid, and the like, or with other oxidizing agents, e.g., hydrogen peroxide, in the presence of a suitable solvent inert under the reaction conditions, e.g., acetic acid, chloroform, and the like. The reaction is conveniently run by mixing the reactants carefully at room temperature (about 20°-25° C.) up to about 40°-50° C., preferably with stirring, and then heating the reaction mixture on a steam bath to ensure completion of the reaction.

The compounds of formula II are prepared by various procedures which are illustrated generally as follows and are further illustrated hereinbelow in the specific exemplary disclosure.

The preparation of the compounds of formula II where $R_1$ and $R_2$ are each hydrogen and Q' is amino is conveniently carried out by heating a pyridinecarboxamidine of the formula, Q-C(=NH)NH$_2$, with a β-(lower-alkoxy)-acrylonitrile, preferably β-ethoxyacrylonitrile to produce the 4-amino-2-Q-pyrimidine.

The preparation of the compounds of formula II where $R_2$ is lower-alkyl and $R_1$ is hydrogen or lower-alkyl are readily produced by reacting a pyridinecarboxamidine of the formula, Q-C(=NH)NH$_2$, with a lower-alkyl β-oxoalkanoate of the formula, $R_2$-COCH($R_1$)—COO—(lower-alkyl) to produce 2-Q-5-$R_1$-6-$R_2$-4-pyrimidinol, reacting the 4-pyrimidinol with a halogenating agent to produce 4-halo-2-Q-5-$R_1$-6-$R_2$-pyrimidine, reacting the 4-halo compound with hydrazine to produce 4-hydrazino-2-Q-5-$R_1$-6-$R_2$-pyrimidine and catalytically hydrogenating the 4-hydrazino compound in the presence of a suitable catalyst, e.g., Raney nickel, to produce 4-amino-2-Q-5-$R_1$-6-$R_2$-pyrimidine.

The preparation of the compounds of formula II where $R_2$ is hydrogen, $R_1$ is methyl and Q' is amino is carried out by reacting a pyridinecarboxamidine of the formula, Q-C(=NH)NH$_2$, with α-piperidinomethylacrylonitrile to produce 4-amino-5-methyl-2-Q-pyrimidine. Optionally, α-piperidinomethylacrylonitrile can be replaced by other α-[(BN)methyl]acrylonitriles where BN is lower-tertiary-amino such as di-(lower-alkyl)amino, e.g., (CH$_3$)$_2$N, (C$_2$H$_5$)$_2$N, and the like, or other saturated N-heteromonocyclic radicals, having 5 or 6 ring atoms, e.g., pyrrolidino, N-methylpiperazino, 2-methylpiperidino, and the like.

The preparation of the compounds of formula II where $R_2$ is hydrogen, $R_1$ is cyano and Q' is amino is carried out by reacting a pyridinecarboxamidine of the formula, Q-C(=NH)NH$_2$, with a (lower-alkoxy)methylenemalononitrile, preferably ethoxymethylenemalononitrile, to produce 4-amino-5-cyano-2-Q-pyrimidine.

The preparation of the compounds of formula II where $R_2$ is hydroxy or hydrogen, $R_1$ is hydrogen or lower-alkyl and Q' is amino are carried out by reacting a pyridinecarboxamidine of the formula, Q-C(=NH)NH$_2$, with a compound of the formula NC-CH($R_1$)COO-(lower-alkyl) to produce 4-amino-6-hydroxy-5-$R_1$-2-Q-pyrimidine, halogenating this 6-hydroxy compound to produce 4-amino-6-halo-5-$R_1$-2-Q-pyrimidine and catalytically hydrogenating the 6-halo, preferably, 6-chloro compound using about 50 p.s.i. of hydrogen in the presence of palladium-on-charcoal catalyst to remove the halo substituent and to produce 4-amino-5-$R_1$-2-Q-pyrimidine.

The intermediate pyridinecarboxamidines of the formula, Q-C(=NH)NH$_2$, are generally known compounds which are prepared by conventional means.

The preparation of the compounds of formula II where Q' is amino and Q is a pyridinyl N-oxide are prepared by reacting the 4-acylamino compounds of formula IV where Q is other than a pyridinyl N-oxide with an oxidizing agent capable of converting pyridines to pyridine-N-oxides by the procedure described above for oxidizing the compounds of formula I where Q is other than a pyridinyl N-oxide to produce the corresponding compounds of formula I where Q is a pyridinyl N-oxide and then hydrolyzing, as illustrated hereinbelow, the 4-acylamino-2-(pyridinyl N-oxide) (IV) to produce the 4-amino-2-(pyridinyl N-oxide) (II).

The compound of formula IV where Q is other than a pyridinyl N-oxide is prepared by acylating the corresponding compound of formula II where Q is other than a pyridinyl N-oxide and Q' is amino, that is, by reacting the said 4-amino compound (II) with a lower-alkanoylating agent or a lower-carbalkoxylating agent, e.g., a lower-alkanoyl halide, preferably chloride, a lower-alkanoic anhydride, a lower-alkyl haloformate, and the like, preferably in the presence of an acid acceptor, as illustrated hereinbelow.

The compound of formula V is prepared by reacting the compound of formula II where Q' is halo, preferably, chloro, with a primary amine $R_6NH_2$ or a secondary amine $R_5R_6NH$ where $R_6$ and $R_5$ are defined as in V. This reaction is conveniently carried out in a lower-alkanol, with or without water; it is preferably run in refluxing ethanol or ethanol-water.

The following examples will further illustrate the invention without, however, limiting it thereto.

A. 4-AMINO-2-(PYRIDINYL)PYRIMIDINES AND INTERMEDIATES

A-1. 4-Amino-2-(4-pyridinyl)pyrimidine - To an ice cold and stirred solution of 172 g. of sodium methoxide in 800 ml. of methanol was slowly added 304 g. of isonicotinamidine dihydrochloride; the resulting mixture was stirred for fifteen minutes and filtered. The inorganic residue was washed with methanol and the filtrate plus washings were evaporated to dryness in vacuo on a steam bath to yield 288 g. of isonicotinamidine in free base form. A mixture of said isonicotinamidine and 150 g. of β-ethoxyacrylonitrile was heated in an oil bath at 130°–150° C. for about four hours, allowing the ethanol formed by the reaction to distill off. The remaining material was dissolved in 200 ml. of concentrated hydrochloric acid and 100 ml. of water, and the solution allowed to stand overnight at room temperature (about 20°–25° C.). The solution was treated with decolorizing charcoal, heated on a steam bath for 30 minutes, filtered and the filtrate basified with ammonium hydroxide. The resulting solid was collected, washed with cold water, air-dried, digested with hot methanol separated and air-dried to yield, as a tan powder, 105 g. of 4-amino-2-(4-pyridinyl)pyrimidine, m.p. 260°–262° C.

The hydrochloride salt of 4-amino-2-(4-pyridinyl)pyrimidine was prepared as follows: a mixture containing 10 g. of 4-amino-2-(4-pyridinyl)pyrimidine, 30 ml. of water and 20 ml. of concentrated hydrochloride acid was warmed to effect solution. To the warm solution was added isopropyl alcohol to turbidity (about 110 ml.) whereupon crystals started to separate. The mixture was cooled and the crystalline precipitate was collected, washed with isopropyl alcohol and ether and dried in vacuo at 80° C. to yield 9.5 g. of 4-amino-2-(4-pyridinyl)pyrimidine dihydrochloride as its monohydrate, m.p. 229° C. with decomposition.

A-2. 4-Amino-2-(3-pyridinyl)pyrimidine, m.p. 157°–159° C., 45 g., was prepared following the procedure described in Example A-1 using 72 g. of nicotinamidine dihydrochloride, 54 g. of sodium methoxide, 400 ml. of methanol, 60 g. of beta-ethoxyacrylonitrile and a heating period of three hours at 100°–125° C.

A-3. 6-Methyl-2-(4-pyridinyl)-4-pyrimidinol - A mixture containing 15.8 g. of isonicotinamidine hydrochloride, 16.8 g. of sodium methoxide, 17 g. of ethyl acetoacetate and 100 ml. of ethanol was refluxed with stirring for seven hours and then evaporated to dryness. The residue was dissolved in water and the aqueous solution made acidic with acetic acid. The resulting solution was collected, washed with water, dried and recrystallized from ethanol to yield 6.7 g. of 6-methyl-2-(4-pyridinyl)-4-pyrimidinol, m.p. 236°–238° C.

A-4. 6-n-Propyl-2-(4-pyridinyl)-4-pyrimidinol - To an ice cooled solution containing 500 ml. of methanol and 16 g. of sodium methoxide was added 47.4 g. of isonicotinamidine hydrochloride; the mixture was stirred for fifteen minutes and filtered to remove the precipitated sodium chloride; the filtrate was concentrated in vacuo; 56 g. of ethyl butrylacetate was added; and the resulting mixture was heated in an oil bath at 160°–180° C. for three hours. After the reaction mixture had been cooled, the separated product was collected and recrystallized from ethanol to yield 38.9 g. of 6-n-propyl-2-(4-pyridinyl)-4-pyrimidinol, m.p. 173°–174° C.

A-5. 4-Chloro-6-methyl-2-(4-pyridinyl)pyrimidine - A mixture containing 26.5 g. of 6-methyl-2-(4-pyridinyl)-4-pyrimidinol, 27 g. of phenylphosphonic dichloride and 75 ml. of phosphorus oxychloride was refluxed for four hours and then poured onto ice. The resulting aqueous mixture was made basic with ammonium hydroxide. The product was extracted from the alkaline mixture using chloroform and the chloroform extract was concentrated in vacuo. The residue was filtered thru a silica gel column using ether as the solvent and eluent. Removal of the ether yielded 12.9 g. of 4-chloro-6-methyl-2-(4-pyridinyl)pyrimidine, m.p. 128°–130° C.

A-6. 4-Hydrazino-6-methyl-2-(4-pyridinyl)pyrimidine - A solution containing 36 g. of 4-chloro-6-methyl-2-(4-pyridinyl)pyrimidine, 100 ml. of ethanol and 20 ml. of hydrazine hydrate was refluxed on a steam bath for two hours and then evaporated to dryness. The residue was partitioned between water and chloroform. The chloroform layer was separated and the chloroform distilled off in vacuo to yield, as a yellow solid, 31.2 g. of 4-hydrazino-6-methyl-2-(4-pyridinyl)pyrimidine, m.p. 150°-152° C., which was used in the following step given in Example A-7. A 3.6 g. portion of this hydrazine was converted into its dicyclohexylsulfamate salt which was recrystallized from ethanol to yield 7.2 g. of said salt, m.p. >280° C. with decomposition.

A-7. 4-Amino-6-methyl-2-(4-pyridinyl)pyrimidine - A mixture containing 31 g. of 4-hydrazino-6-methyl-2-(4-pyridinyl)-pyrimidine, 150 ml. of ethanol and 2 g. of Raney nickel was shaken under hydrogen (48 p.s.i.) and heated to 63° C. whereupon there was an uptake of 10.7 lbs. of hydrogen. The reaction mixture was cooled to room temperature and the catalyst was filtered off. The filtrate was concentrated in vacuo to yield an orange solid that was crystallized from isopropyl alcohol to yield, as tan crystals, 22.6 g. of 4-amino-6-methyl-2-(4-pyridinyl)pyrimidine, m.p. 192°-194° C.

A-8. 4-Amino-5-methyl-2-(4-pyridinyl)pyrimidine - A mixture containing 15.8 g of isonicotinamidine hydrochloride, 100 ml. of ethanol, 5.4 g. of sodium methoxide and 16.8 g. of α-(piperidinomethyl)acrylonitrile was stirred at room temperature for two hours and then refluxed overnight (about sixteen hours). The reaction mixture was then cooled and evaporated to dryness in vacuo. The residue was diluted with water and the solid was collected, washed with water and recrystallized from isopropyl alcohol to yield 5.7 g. of 4-amino-5-methyl-2-(4-pyridinyl)pyrimidine, m.p. 224°-226° C. It was crystallized as its dimethanesulfonate, m.p. 210°-213° C., 6.5 g., by dissolving it in a minimum of hot isopropyl alcohol, adding 6.6 ml. of methanesulfonic acid, cooling the mixture, collecting the precipitated salt and drying it in vacuo at 80° C.

A-9. 4-Amino-2-(2-pyridinyl)pyrimidine - A mixture containing 12.2 g. of 2-pyridinecarboxamidine in 9.8 g. of β-ethoxyacrylonitrile was heated in an oil bath at 150°-160° C. for 3 hours. The solid residue was taken up in boiling iosopropyl alcohol, the hot solution treated with decolorizing charcoal and filtered. To the hot filtrate was added 21 g. of methanesulfonic acid and the mixture chilled. The separated salt was recrystallized twice from isopropanol-ethanol and once from ethanol to yield 11.8 g. of 4-amino-2-(2-pyridinyl)-pyrimidine as its dimethanesulfonate, m.p. 184°-186° C.

Following the procedure described in Example A-1 but using in place of isonicotinamidine a molar equivalent quantity of the appropriate pyridine carboxamidine, i.e., Q-C(=NH)NH$_2$, the 4-amino-2-Q-pyrimidines of Examples A-10 through A-13 are obtained:

A-10 . 4-Amino-2-(2-methyl-4-pyridinyl)pyrimidine using 2-methylisonicotinamidine.

A-11. 4-Amino-2-(3-methyl-4-pyridinyl)pyrimidine using 3-methylisonicotinamidine.

A-12. 4-Amino-2-(2-ethyl-4-pyridinyl)pyrimidine using 2-ethylisonicotinamidine.

A-13. 4-Amino-2-(2,6-dimethyl-4-pyridinyl)pyrimidine using 2,6-dimethylisonicotinamidine.

A-14. 4-Amino-2-(4pyridinyl)-6-pyrimidinol (alternatively named as 6-amino-2-(4-pyridinyl)-4-pyrimidinol) - A mixture containing 15.6 g. of isonicotinamidine hydrochloride, 11.3 g. ethyl cyanoacetate, 10.8 g. of sodium methoxide and 100 ml. of ethanol was stirred at room temperature for 30 minutes and then refluxed for seven hours, followed by evaporation to dryness. To the residue was added 100 ml. of water and the mixture was then acidified by adding acetic acid. The solid was collected, dried in vacuo at 80° C. slurried in 100 ml. boiling ethanol and collected to yield 9.6 g. of 4-amino-2-(4-pyridinyl)-6-pyrimidinol, m.p. >350° C.

A-15. 4-Amino-2-(4-pyridinyl)-5-pyrimidinecarbonitrile - To a stirred solution containing 15.8 g. of isonicotinamidine hydrochloride, 6 g. of sodium methoxide and 200 ml. of methanol was added 14.2 g. of ethoxymethylenemalononitrile and the resulting mixture was stirred at room temperature overnight (about sixteen hours). The solid was collected, washed with water and recrystallized from methanol to yield 20.7 g. of 4-amino-2-(4-pyridinyl)-5-pyrimidinecarbonitrile, m.p. 253°-255° C.

A-16. N-[2-(4-Pyridinyl)-4-pyrimidinyl]acetamide - A mixture containing 7 g. of 4-amino-2-(4-pyridinyl)-pyrimidine, 25 ml. of pyridine and 10 ml. of acetic anhydride was allowed to stand at room temperature overnight, and then boiled on a hot plate until all of the solid had dissolved. The reaction mixture was cooled to room temperature and poured onto ice. After the ice had melted, the white crystalline solid was collected, washed with water, dried in vacuo at 80° C. and recrystallized from ethanol to produce 3.8 g. of N-[2-(4-pyridinyl)-4-pyrimidinyl]acetamide, m.p. 218°-220° C.

A-17. N-[2-(4-Pyridinyl)-4-pyrimidinyl]hexanamide - A mixture containing 4 g. of 4-amino-2-(4-pyridinyl)-pyrimidine, 5 g. of n-hexanoyl chloride and 50 ml. of pyridine was allowed to stand at room temperature overnight and then poured onto the ice. After the ice had melted, 10 ml. of concentrated ammonium hydroxide was added and the cream colored solid was collected, washed with water, dried in vacuo and recrystallized from isopropyl alcohol to yield 6.2 g. of N-[2-(4-pyridinyl)-4-pyrimidinyl]hexanamide, m.p. 119°-120° C.

A-18. 2-Methyl-N-[2-(4-pyridinyl)-4-pyrimidinyl]-propanamide - A mixture containing 8.6 g. of 4-amino-2-(4-pyridinyl)pyrimidine, 50 ml. of pyridine and 10 ml. of isobutyryl chloride was allowed to stand at room temperature overnight and then poured into ice cold water. The solid was collected, washed with water, dried in vacuo at 80° C. and recrystallized from ethanol to yield 7.9 g. of 2-methyl-N-[2-(4-pyridinyl)-4-pyrimidinyl]-propanamide, m.p. 215°-217° C.

A-19. n-Butyl N-[2-(4-pyridinyl)-4-pyrimidinyl]-carbamate - A mixture containing 9 g. of 4amino-2-(4-pyridinyl)-pyrimidine, 10 ml. of n-butyl chloroformate and pyridine was kept in an ice bath for one hour and then at room temperature overnight. The reaction mixture was then poured into ice cold water; the solid was collected, washed with water, dried in vacuo at 80° C. and recrystallized from acetonitrile to yield 11.2 g. of n-butyl N-[2-(4-pyridinyl)-4-pyrimidinyl]carbamate, m.p. 180°-182° C.

A-20. Ethyl N-[2-(4-pyridinyl)-4-pyrimidinyl]carbamate as its methanesulfonate, m.p. 198°-200° C., is obtained following the procedure described in Example A-19 but using in place of n-butyl chloroformate a molar equivalent quantity of ethyl chloroformate, and recrystallization from ethanol.

A-21. n-Butyl N-[2-(4-pyridinyl)-4-pyrimidinyl]carbamate N-Oxide [It will be appreciated, in view of the definition of Q in formula I hereinabove, that N-oxide as used here and elsewhere in naming claimed compounds of the invention means the N-oxide of the 2-pyridinyl) substituent, specifically the N-oxide of the 2-(4-pyridinyl) substituent in this Example A-21.] - To an ice cold solution containing 6 g. of n-butyl N-[2-(4-pyridinyl)-4-pyrimidinyl]carbamate and 100 ml. of chloroform was added 4.9 g. of 85% m-chloroperbenzoic acid and the resulting solution was allowed to stand at room temperature overnight. The excess acid was extracted with aqueous potassium carbonate and the remaining organic solution was collected to yield 5.8 g. of n-butyl N-[2-(4-pyridinyl)-4-pyrimidinyl]carbamate N-oxide which was combined with 1.9 g. of the same compound prepared in another run and the combined 7.7 g. of this compound was used without any further purification in the following Example A-22.

A-22. 4-Amino-2-(4-pyridinyl)pyrimidine N-Oxide - A mixture containing 7.7 g. of n-butyl N-[2-(4-pyridinyl)-4-pyrimidinyl]carbamate N-oxide, 50 ml. of ethanol and 10 ml. of 35% aqueous sodium hydroxide solution was allowed to stand at room temperature over the weekend and then was refluxed for four hours, concentrated in vacuo and the concentrate acidified with acetic acid. The mixture was heated on a steam bath and made basic by adding ammonium hydroxide solution. The crystalline solid was collected, washed with water, dried in vacuo at 80° C. and recrystallized from dimethylformamide to yield 3.2 g. of 4-amino-2-(4-pyridinyl)pyrimidine N-oxide, m.p. 317°-320° C.

4-Amino-2-(4-pyridinyl)-4-pyrimidine N-oxide also is prepared following the above procedure of Example A-22 but using in place of n-butyl N-[2-(4-pyridinyl)-4-pyrimidinyl]carbamate N-oxide a molar equivalent quantity of N-[2-(4-pyridinyl)-4-pyrimidinyl]acetamide N-oxide or ethyl N-[2-(4-pyridinyl)-4-pyrimidinyl]carbamate N-oxide.

A-23. N-(1,1-Dimethylethyl)-2-(4-pyridinyl)-4-pyrimidinamine [alternatively can be named 4-tert.-butylamino)-2-(4-pyridinyl)pyrimidine] - A mixture containing 10.2 g. of 4chloro-2-(4-pyridinyl)pyrimidine, 15 ml. of tert.-butylamine and 50 ml. of ethanol was refluxed for four hours and then concentrated in vacuo to remove the solvent and other volatile materials. The residue was partitioned between chloroform and aqueous ammonium hydroxide solution. The chloroform layer was separated and the chloroform removed in vacuo. The remaining residue was dissolved in ether containing 2 to 5% (v/v) methanol and the solution was passed through a silica gel column. The filtrate was evaporated in vacuo to remove the solvents and the residue was crystallized from cyclohexane to yield 7.1 g. of N-(1,1-dimethylethyl)-2-(4-pyridinyl)-4-pyrimidinamine, m.p. 202°-204° C.

A-24. N,N-Dimethyl-2-(4-pyridinyl)-4-pyrimidinamine - A mixture containing 6 g. of 4-chloro-2-(4-pyridinyl)pyrimidine, 10 ml of 70% aqueous dimethylamine and 50 ml. of ethanol was refluxed for four hours and then evaporated to dryness. The residue was partitioned between aqueous sodium bicarbonate solution and chloroform. The chloroform layer was separated, dried over anhydrous magnesium sulfate, concentrated in vacuo to remove the chloroform and the residue, and recrystallized from cyclohexane to yield 4.8 g. of N,N-dimethyl-2-(4-pyridinyl)-4-pyrimidinamine, m.p. 109°-110° C.

A-25. N,N,6-Trimethyl-2-(4pyridinyl)-4-pyrimidinamine as its dihydrochloride monohydrate, m.p. 274°-276° C., 7.2 g. was prepared following the procedure described in Example A-24 using 8 g. of 4-chloro-6-methyl-2-(4-pyridinyl)pyrimidine, 15 ml. of 60% aqueous dimethylamine, 500 ml. of ethanol, a refluxing period of 2 hours and crystallization of the dihydrochloride from ethanol.

A-26. N,6-Dimethyl-2-(4-pyridinyl)-4-pyrimidinamine, m.p. 145°-146° C., 7.6 g. was prepared following the procedure described in Example A-24 using 8 g. of 4-chloro-6-methyl-2-(4-pyridinyl)pyrimidine, 15 ml. of 40% aqueous methylamine, 50 ml. of ethanol, a refluxing period of two hours and recrystallization from ether-n-hexane.

A-27. 4-Amino-6-n-propyl-2-(4-pyridinyl)pyrimidine is prepared following the procedure described in Examples A-5, A-6 and A-7 starting with a molar equivalent quantity of 6-n-propyl-2-(4-pyridinyl)-4-pyrimidinol in place of 6-methyl-2-(4pyridinyl)-4-pyrimidinol to produce respectively 4-chloro-6-n-propyl-2-(4-pyridinyl)-pyrimidine, 4-hydrazino-6-n-propyl-2-(4-pyridinyl)-pyrimidine and 4-amino-6-n-propyl-2-(4-pyridinyl)-pyrimidine.

A-28. N-[2-(4-pyridinyl)-4-pyrimidinyl]acetamide N-Oxide is obtained following the procedure described in Example A-21 using a molar equivalent quantity of N-[2-(4-pyridinyl)-4-pyrimidinyl]acetamide in place of n-butyl N-[2-(4-pyridinyl)-4-pyrimidinyl]carbamate.

A-29. Ethyl N-[2-(4-pyridinyl)-4-pyrimidinyl]carbamate N-Oxide is obtained following the procedure described in Example A-21 using a molar equivalent quantity of ethyl N-[2-(4-pyridinyl)-4-pyrimidinyl]carbamate in place of n-butyl N-[2-(4-pyridinyl)-4-pyrimidinyl]carbamate.

Following the procedure described in Example A-23 using in place of tert.-butylamine a molar equivalent quantity of the appropriate amine of the formula $NHR_5R_6$, the compounds of Examples A-30 through A-33 are obtained:

A-30. N,N-Dimethyl-2-(4-pyridinyl)-4-pyrimidinamine using diethylamine.

A-31. N-Ethyl-2-(4-pyridinyl)-4-pyrimidinamine using ethylamine.

A-32. N,N-bis(2-Hydroxyethyl)-2-(4-pyridinyl)-4-pyrimidinamine using bis(2-hydroxyethyl)amine.

A-33. N-(2-Hydroxyethyl)-2-(4-pyridinyl)-4-pyrimidinamine using 2-hydroxyethylamine.

A-34. N,N-Diethyl-6-methyl-2-(4-pyridinyl)-4-pyrimidinamine - A mixture containing 8.2 g. of 4-chloro-6-methyl-2-(4-pyridinyl)pyrimidine, 8.7 g. of diethylamine hydrochloride, 100 ml. of ethanol, 6 g. of potassium carbonate and 10 ml. of water was refluxed with stirring for eight hours and then concentrated in vacuo to dryness. The residue was swirled in water and the solid collected. The solid was dissolved in boiling isopropyl alcohol, the hot solution treated with decolorizing charcoal and filtered, and the hot filtrate allowed to cool. The filtrate was then saturated with gaseous hydrogen chloride, ether was added to turbidity and the mixture was allowed to stand. The separated solid was collected and dried in vacuo at 80° C. to yield 7.4 g. of N,N-diethyl-6-methyl-2-(4pyridinyl)-4-pyrimidinamine dihydrochloride, m.p. 205°-208° C.

A-35. N,N-bis(2-Hydroxyethyl)-6-methyl-2-(4-pyridinyl)-pyrimidinamine - A solution containing 8.2 g. of 4-chloro-6-methyl-2-(pyridinyl)pyrimidine, 12 g. of bis(2-hydroxyethyl)amine and 100 ml. of ethanol was refluxed for forty hours and the ethanol was then removed in vacuo. To the residue was added 100 ml. of water, the resulting cloudy solution was filtered and the filtrate extracted with six 200 ml. portions of chloroform. The chloroform solution was evaporated in vacuo to remove the chloroform and the remaining solid was crystallized from isopropyl alcohol-ether to yield 7.5 g. of N,N-bis(2-hydroxyethyl)-6-methyl-2-(4-pyridinyl)-pyrimidinamine, m.p.135°–137° C.

A-36. tert.-Butyl N-[2-(4-pyridinyl)-4-pyrimidinyl]-carbamate is prepared following the procedure described in Example A-19 but using in place of n-butyl chloroformate a molar equivalent quantity of tert.-butyl azido formate.

B. DI-(LOWER-ALKYL) [2-(PYRIDINYL)-4-PYRIMIDINYL]AMINO-METHYLENEMALONATES AND ANALOGS

B-1. Diethyl N-[2-(4-pyridinyl)-4-pyrimidinyl]aminomethylenemalonate - A mixture containing 108 g. of 4-amino-2-(4-pyridinyl)pyrimidine, 180 g. of diethyl ethoxymethylenemalonate and 300 ml. of xylene was heated with stirring in an oil bath at 190°–195° C. for seventy-two hours, while allowing the ethanol (formed by the reaction) and xylene solvent to evaporate by using an air cooled condenser. The oily residue was treated with 500 ml. of ethanol followed by decolorizing charcoal. The mixture was filtered and the filtrate evaporated to dryness in vacuo. The residue was crystallized from ethanol-ether to give 130 g. of diethyl N-[2-(4-pyridinyl)-4-pyrimidinyl]aminomethylenemalonate, m.p. 138°–140° C. This compound was also prepared in the absence of a solvent as follows: a mixture containing 100 g. of 2-amino-4-(4-pyridinyl)pyrimidine and 190 g. of diethyl ethoxyaminomethylenemalonate was heated with stirring for twenty hours at 135°–143° C. and was then allowed to cool slowly. Crystallization started when the temperature was above 80° C. whereupon 100 ml. of absolute ethanol was added. The mixture was then allowed to cool to room temperature and the crystalline precipitate was collected, washed with cold ethanol and then ether. The resulting tan crystalline material was recrystallized from 400 ml. of absolute ethanol using decolorizing charcoal to yield, as yellow crystals, 105 g. of diethyl N-[2-(4-pyridinyl)-4-pyrimidinyl]aminomethylenemalonate, m.p. 143°–145° C. A 45 g. portion of this compound was dissolved in 225 mol. of isopropyl alcohol, treated with decolorizing charcoal and filtered. To the filtrate was added one equivalent of concentrated hydrochloric acid whereupon the crystallized hydrochloride separated immediately. The mixture was cooled and the product was collected, washed successively with cold isopropyl alcohol and ether, and dried in vacuo at 80° C. to yield 48 g. of diethyl N-[2-(4-pyridinyl)-4-pyrimidinyl]-aminomethylenemalonate hydrochloride, m.p. 227°–230° C. with decomposition.

B-2. Diethyl N-[2-(3-pyridinyl)-4-pyrimidinyl]-]aminomethylenemalonate - A mixture containing 44 g. of 4-amino-2-(3-pyridinyl)pyrimidine and 55 g. of diethyl ethoxymethylenemalonate was heated in an oil bath at 160°–170° C. for three hours and then cooled to room temperature. The reaction mixture was dissolved in methylene dichloride and the solution filtered thru a column of silica gel followed by elution of the column with 10% methanol in ether. Evaporation of the eluate yielded a yellow solid which was recrystallized from ether-isopropyl alcohol to yield 45 g. of diethyl N-[2-(3-pyridinyl)-4-pyrimidinyl]aminomethylenemalonate, m.p. 115°–117° C.

B-3. Dimethyl N-[2-(4-pyridinyl)-4-pyrimidinyl]-aminomethylenemalonate - A mixture containing 10 g. of 4-amino-2-(4-pyridinyl)pyrimidine, 10 g. of dimethyl methoxymethylenemalonate and 750 ml. of xylene was refluxed with stirring for fourteen hours and then filtered to remove any insoluble reddish residue. The solution was evaporated to dryness; the residue was dissolved in 400 ml. of 50–50 mixture (v/v) of methanol-chloroform; and, the solution was treated with decolorizing charcoal and filtered. The filtrate was concentrated to a volume of about 200 ml. and was allowed to cool. The resulting yellow precipitate was collected, washed with methanol and dried in vacuo to 80° C. to give 14.2 g. of dimethyl N-[2-(4-pyridinyl)-4-pyrimidinyl]aminomethylenemalonate, m.p. 209°–211° C.

B-4. Dimethyl N-[2-(3-pyridinyl)-4-pyrimidinyl]-aminomethylenemalonate - A mixture containing 8.6 g. of 4-amino-2-(3-pyridinyl)pyrimidine and 15 g. of dimethyl ethoxymethylenemalonate was heated in an oil bath at 140°–150° C. for four hours. The reaction mixture was then dried in vacuo and the remaining oily residue was dissolved in methanol. The methanol solution was treated with decolorizing charcoal and filtered. The filtrate was chilled and the separated solid was collected and dried in vacuo at 80° C. to yield 11.8 g. of dimethyl N-[2-(3-pyridinyl)-4-pyrimidinyl]-aminomethylenemalonate, m.p. 183°–184° C.

B-5. Diethyl N-[6-methyl-2-(4-pyridinyl)-4-pyrimidinyl]aminomethylenemalonate - A mixture containing 15.2 g. of 4-amino-6-methyl -2-(4-pyridinyl)-pyrimidine and 25 ml. of diethyl ethoxymethylenemalonate was heated with stirring at 150°–160° C. for two hours and then allowed to cool. The separated product was collected and crystallized from methanol to yield 22.6 g. of diethyl N-[6-methyl-2-(4-pyridinyl)-4-pyrimidinyl]aminomethylenemalonate, m.p. 169°–171° C.

Following the procedure described above in Example B-1 but using in place of diethyl ethoxymethylenemalonate a molar equivalent quantity of the appropriate di-(lower-alkyl) lower-alkoxy)methylenemalonate, the compounds of Examples B-6 through B-10 are obtained:

B-6. Di-n-propyl N-[2-(4-pyridinyl)-4-pyrimidinyl]-aminomethylenemalonate using di-n-propyl n-propoxymethylenemalonate.

B-7. Diisopropyl N-[2-(4-pyridinyl)-4-pyrimidinyl]-aminomethylenemalonate using diisopropyl isopropoxymethylenemalonate.

B-8. Di-n-butyl N-[2-(4-pyridinyl)-4-pyrimidinyl]-aminomethylenemalonate using di-n-butyl n-butoxymethylenemalonate.

B-9. Diisobutyl N-[2-(4-pyridinyl)-4-pyrimidinyl]-aminomethylenemalonate using diisobutyl ethoxymethylenemalonate.

B-10. Di-n-hexyl N-[2-(4-pyridinyl)-4-pyrimidinyl]-aminomethylenemalonate using di-n-hexyl n-hexoxymethylenemalonate.

Following the procedures described in Example B-1 but using in place of 4-amino-2-(4-pyridinyl)pyrimidine a molar equivalent quantity of the appropriate 4-amino-2-Q-pyrimidine, the compounds of Examples B-11 through B-14 are obtained:

B-11. Diethyl N-[2-(2-methyl-4-pyridinyl)-4-pyrimidinyl]aminomethylenemalonate using 4-amino-2-(2-methyl-4-pyridinyl)pyrimidine. B-12. Diethyl N-[2-(3-methyl-4-pyridinyl)-4-pyrimidinyl]aminomethylenemalonate using 4-amino-2-(3-methyl-4-pyridinyl)pyrimidine.

B-13. Diethyl N-[2-(2-ethyl-4-pyridinyl)-4-pyrimidinyl]aminomethylenemalonate using 4-amino-2-(2-ethyl-4-pyridinyl)pyrimidine.

B-14. Diethyl N-[2-(2,6-dimethyl-4-pyridinyl)-4-pyrimidinyl]aminomethylenemalonate using 4-amino-2-(2,6-dimethyl-4-pyridinyl)pyrimidine.

B-15. Diethyl N-[2-(2-pyridinyl)-4-pyrimidinyl]-aminomethylenemalonate - A mixture containing 8.7 g. of 4-amino-2-(2-pyridinyl)pyrimidine and 14.2 g. of diethyl ethoxymethylenemalonate was heated in an oil bath at 130°-140° C. for one hour and then cooled to room temperature. To the cooled reaction mixture was added with stirring 300 ml. of ether and the mixture was filtered. To the filtrate was added 4.8 g. of methanesulfonic acid dissolved in 25 ml. of ethanol whereupon there separated an oily material which became a crystalline solid on standing. The solid was collected and recrystallized from ether-ethanol to yield 10.4 g. of diethyl N-[2-(2-pyridinyl)-4-pyrimidinyl]aminomethylenemalonate methanesulfonate, m.p. 162°-164° C.

B-16. Diethyl N-[2-(4-pyridinyl)-4-pyrimidinyl]-aminomethylenemalonate N-Oxide - A mixture containing 5.2 g. of diethyl N-[2-(4-pyridinyl)-4-pyrimidinyl]-aminomethylenemalonate, 3.5 g. of m-chloroperbenzoic acid (85%) and 125 ml. of methylene dichloride was stirred in an ice bath for about one hour and then at room temperature (about 20°-25° C.) overnight (about 16 hours). An equal volume of chloroform was added and this mixture was washed with aqueous sodium bicarbonate solution. The organic layer was separated, dried over anhydrous magnesium sulfate and evaporated in vacuo to yield a yellow solid. The solid was recrystallized from ethanol to yield 3.5 g. of diethyl N-[2-(4-pyridinyl)-4-pyrimidinyl]aminomethylenemalonate N-oxide, m.p. 198°-201° C. (started shrinking about 180° C.).

Alternatively, diethyl N-[2-(4-pyridinyl)-4-pyrimidinyl]aminomethylenemalonate N-oxide is prepared following the procedure of Example B-1 using a molar equivalent quantity of 4-amino-2-(4-pyridinyl)-pyrimidine N-oxide (see Example A-22 for preparation) in place of 4-amino-2-(4-pyridinyl)pyrimidine.

B-17. Ethyl α-{[2-(4-pyridinyl)-4-pyrimidinyl]-aminomethylene}acetoacetate (alternatively named ethyl 3-oxo-2-{[2-(4-pyridinyl)-4-pyrimidinyl]aminomethylene}butanoate) - A mixture containing 8.6 g. of 4-amino-2-(4-pyridinyl)pyrimidine, 13 g. of ethyl acetoacetate, 15 g. of triethyl orthoformate, 100 g. of p-toluenesulfonic acid and 700 ml. of xylene was refluxed with stirring for 92 hours, cooled to room temperature and then filtered. The filtrate was evaporated to dryness and the residue was dissolved in boiling ethanol-chloroform and the hot solution treated with decolorizing charcoal and filtered. The filtrate was concentrated to about one-half of its volume and then cooled. The separated solid was collected, washed with ethanol and dried in vacuo at 80° C. to yield 7.2 g. of ethyl α-{[2-(4-pyridinyl)-4-pyrimidinyl]aminomethylene}acetoacetate, m.p. 198°-200° C.

B-18. Ethyl α-cyano-α-{[2-(4-pyridinyl)-4-pyrimidinyl]aminomethylene}acetate (alternatively named ethyl 2-cyano-3-{[2-(4-pyridinyl)-4-pyrimidinyl]amino}-2-propenoate) - A stirred mixture containing 10 g. of 4-amino-2-(4-pyridinyl)-pyrimidine, 13 g. of ethyl α-cyano-α-ethoxymethyleneacetate and 700 ml. of xylene was refluxed for 72 hours, treated with decolorizing charcoal and filtered. The filtrate was evaporated to dryness and the yellow crystalline solid residue was recrystallized twice from ethanol to yield 9.3 g. of ethyl α-cyano-α-{[2-(4-pyridinyl)-4-pyrimidinyl]aminomethylene}acetate, m.p. 195°-197° C.

B-19. Ethyl 2-cyano-3-{[2-(4-pyridinyl)-4-pyrimidinyl]-amino}-2-butenoate - A mixture containing 8 g. of 4-amino-2-(4-pyridinyl)pyrimidine, 12 g. of ethyl 2-cyano-3-ethoxy-2-butenoate and 700 ml. of xylene was refluxed with stirring for seventy-two hours. The reaction mixture was treated with decolorizing charcoal and filtered. The filtrate was evaporated in vacuo to dryness. The residue was treated with methylene dichloride and the insoluble starting amine was filtered off. The filtrate was chromatographed on a silica gel column (400 g.) using 20% methanol-ether (v/v) as the eluent. Evaporation in vacuo of the eluate yielded a crystalline material which was recrystallized from ethanol to yield 2.8 g. of ethyl 2-cyano-3-{[2-(4-pyridinyl)-4-pyrimidinyl]amino}-2-butenoate, m.p. 203°-205° C.

B-20. 3-<{[2-(4-Pyridinyl)-3-pyrimidinyl]amino}methylene>-2,4-pentanedione - A mixture containing 8.6 g. of 4-amino-2-(4-pyridinyl)pyrimidine, 10.7 g. of 2,4-pentanedione, 15 g. of triethyl orthoformate, 100 mg. of p-toluenesulfonic acid monohydrate and 700 ml. of xylene was refluxed with stirring for 98 hours, cooled to room temperature and filtered. The filtrate was evaporated in vacuo and the remaining residue was dissolved in boiling ethanol, treated with decolorizing charcoal and the material filtered. The filtrate was concentrated and cooled. The remaining yellow crystalline precipitate was collected, washed with ethanol and dried in vacuo at 80° C. to yield 6.9 g. of 3-<{[2-(4-pyridinyl)-3-pyrimidinyl]amino}methylene>-2,4-pentanedione, m.p. 182°-183° C.

B-21. 2,2-Dimethyl-5-<{[2-(4-pyridinyl)-4-pyrimidinyl]-amino}-methyl>-1,3-dioxane-2,4-dione - A mixture containing 8.6 g. of 4-amino-2-(4-pyridinyl)-pyrimidine, 15 g. of cyclic isopropylidene malonate, 15 g. of triethyl orthoformate, 100 mg. of p-toluenesulfonic acid monohydrate and 700 ml. of xylene was refluxed with stirring for one-hundred and forty-four hours and cooled. The separated solid was collected, washed with ethanol and recrystallized from dimethylformamide to yield 12 g. of 2,2-dimethyl-5-<{[2-(4-pyridinyl)-4-pyrimidinyl]amino}-methyl>-1,3-dioxane-2,4-dione, m.p. 240° C. with decomposition.

B-22. Diethyl N-[5-methyl-2-(4-pyridinyl)-4-pyrimidinyl]aminomethylenemalonate is prepared following the procedure described in Example B-1 using a molar equivalent quantity of 4-amino-5-methyl-2-(4-pyridinyl)pyrimidine in place of 4-amino-2-(4-pyridinyl)pyrimidine.

B-23. Diethyl N-[6-n-propyl-2-(4-pyridinyl)-4-pyrimidinyl]aminomethylenemalonate is prepared following the procedure described in Example B-1 using a molar equivalent quantity of 4-amino-5-n-propyl-2-(4-pyridinyl)pyrimidine in place of 4-amino-2-(4-pyridinyl)pyrimidine.

B-24. N-[2-(4-Pyridinyl)-4-pyrimidinyl]aminomethylenemalononitrile is prepared following the procedure described in Example B-18 using a molar equivalent quantity of ethoxymethylenemalononitrile in place of ethyl α-cyano-α-ethoxymethyleneacetate.

B-25. N-[2-(4-Pyridinyl)-4-pyrimidinyl]aminomethylenemalonamide is prepared following the procedure described in Example B-17 using a molar equivalent quantity of malonamide in place of ethyl acetoacetate.

B-26. α-{[2-(4-Pyridinyl)-4-pyrimidinyl]aminomethylene}acetoacetamide is prepared following the procedure described in Example B-17 using a molar equivalent quantity of acetoacetamide in place of ethyl acetoacetate.

B-27. Ethyl α-carbamyl-α-{[2-(4-pyridinyl)-4-pyrimidinyl]aminomethylene}acetate is prepared following the procedure described in Example B-17 using a molar equivalent quantity of ethyl α-carbamylacetate in place of ethyl acetoacetate.

B-28. α-Cyano-α-{[2-(4-pyridinyl)-4-pyrimidinyl]aminomethylene}acetamide is prepared following the procedure described in Example B-17 using a molar equivalent quantity of α-cyanoacetamide in place of ethyl acetoacetate.

B-29. Methyl α-cyano-α-{[2-(4-pyridinyl)-4-pyrimidinyl]aminomethylene}acetate is obtained following the procedure described in Example B-17 using a molar equivalent quantity of methyl α-cyanoacetate in place of ethyl acetoacetate.

B-30. 3-{[2-(4-Pyridinyl)-4-pyrimidinyl]amino}-2-propenenitrile - A mixture containing 17.2 g. of 4-amino-2-(4-pyridinyl)pyrimidine, 75 ml. of dimethyl sulfoxide, 4.8 g. of 57% sodium hydride and 12 ml. of β-ethoxyacrylonitrile was stirred at room temperature for five hours and then poured into ice cold water. The separated solid was collected, washed with water, dried in vacuo at 80° C. and recrystallized from dimethylformamide to produce 18.3 g. of 3-{[2-(4-pyridinyl)-4-pyrimidinyl]amino}-2-propenenitrile, m.p. 253°–255° C.

B-31. Methyl 3-{[2-(4-pyridinyl)-4-pyrimidinyl]amino}-2-propenoate is prepared following the procedure described in Example B-30 using a molar equivalent quantity of methyl β-methoxyacrylate in place of β-ethoxyacrylonitrile.

B-32. Ethyl 3-{[2-(4-pyridinyl)-4-pyrimidinyl]amino}-2-propenoate is prepared following the procedure described in Example B-30 using a molar equivalent quantity of ethyl β-methoxyacrylate in place of β-ethoxyacrylonitrile.

B-33. 3-{[2-(4-Pyridinyl)-4-pyrimidinyl]amino}-2-propenamide is obtained following the procedure described in Example B-30 using a molar equivalent quantity of β-ethoxyacrylamide in place of β-ethoxyacrylonitrile.

B-34. Diethyl N-[6-hydroxy-2-(4-pyridinyl)-4-pyrimidinyl]aminomethylenemalonate is prepared following the procedure described in Example B-1 using a molar equivalent quantity of 4-amino-6-hydroxy-2-(4-pyridinyl)pyrimidine in place of 4-amino-2-(4-pyridinyl)pyrimidine.

B-35. Diethyl N-[6-hydroxy-5-methyl-2-(4-pyridinyl)-4-pyrimidinyl]aminomethylenemalonate is obtained following the procedure described in Example B-1 using a molar equivalent quantity of 4-amino-6-hydroxy-5-methyl-2-(4-pyridinyl)pyrimidine in place of 4-amino-2-(4-pyridinyl)pyrimidine.

B-36. Diethyl N-[5-ethyl-6-hydroxy-2-(4-pyridinyl)-4-pyrimidinyl]aminomethylenemalonate is obtained following the procedure described in Example B-1 using a molar equivalent quantity of 4-amino-5-ethyl-6-hydroxy-2-(4-pyridinyl)pyrimidine in place of 4-amino-2-(4-pyridinyl)pyrimidine.

B-37. Diethyl N-[6-chloro-5-ethyl-2-(4-pyridinyl)-4-pyrimidinyl]aminomethylenemalonate is obtained following the procedure described in Example A-5 using a molar equivalent quantity of diethyl N-[5-ethyl-6-hydroxy-2-(4-pyridinyl)-4-pyrimidinyl]aminomethylenemalonate in place of 6-methyl-2-(4-pyridinyl)-4-pyrimidinol.

B-38. Diethyl N-[5-ethyl-2-(4-pyridinyl)-4-pyrimidinyl]aminomethylenemalonate is obtained by reacting diethyl N-[6-chloro-5-ethyl-2-(4-pyridinyl)-4-pyrimidinyl]-aminomethylenemalonate in absolute ethanol with 50 p.s.i. of hydrogen under catalytic hydrogenation conditions using palladium-on-charcoal, thereby removing the 6-chloro substituent of the starting material.

B-39. Diethyl N-[5-cyano-2-(4-pyridinyl)-4-pyrimidinyl]-aminomethylenemalonate is obtained following the procedure described in Example B-1 using a molar equivalent quantity of 4-amino-5-cyano-2-(4-pyridinyl)pyrimidine [same as 4-amino-2-(4-pyridinyl)-5-pyrimidinecarbonitrile] in place of 4-amino-2-(4-pyridinyl)pyrimidine.

B-40. α-{[2-(4-Pyridinyl)-4-pyrimidinyl]aminomethylene}acetonitrile is obtained following the procedure described in Example B-17 using a molar equivalent quantity of acetoacetonitrile in place of ethyl acetoacetate.

B-41. N-[2-(4-Pyridinyl)-4-pyrimidinyl]-3-oxo-2-butenylamine is prepared following the procedure described in Example B-30 using a molar equivalent quantity of methyl methoxyvinyl ketone of the formula $CH_3OCH=CHCOCH_3$ in place of β-ethoxyacrylonitrile.

The anti-allergic activity of the compounds of formulas I, II (except where Q' is halo), IV (as noted above) and V is determined by showing their effectiveness as inhibitors of release of mediators of allergic reactions by the IgE-mediated passive cutaneous anaphylaxis (PCA) method described as follows (IgE is the abbreviation for Immuno-globulin E, the cell-sensitizing antibody): Sprague-Dawley rats weighing 70 to 90 grams each are injected intradermally with multiple serial dilutions of IgE 48 hours before administration of the drug. The rats are fasted overnight (approximately seventeen hours) before the drug administration. Each drug being tested is administered orally at 100 mg./kg. to each of four rats. Six other rats are observed as a control group. One hour after drug administration, 10 mg./kg. of egg albumen was administered intravenously together with 17 mg./kg. of Evans Blue. Thirty minutes later, the rats are killed by cervical fracture, the i.d. injected skin is everted, and the average of two perpendicular diameters of each blue area is recorded. The average diameters vs. the reciprocal of the dilution of antibody in the control group is plotted on a semilog graph, and a best-fitting line is drawn through points for the control rats, and a best-fitting parallel line to the control line is drawn for each tested drug. Comparative drug activity is evaluated by the degree of the shift to the right from controls, that is, by the ratio, R, of:

$$R = \frac{\text{reciprocal of antibody dilution necessary for zero mm. diameter in control group}}{\text{reciprocal of antibody dilution necessary for zero mm. diameter in medicated group}}$$

The results are interpreted as follows:

| R(= degree of shift to the right | Interpretation of Drug Activity |
|---|---|
| 1.0 – 2.0 | Inactive |
| 2 – 4 | Weak |
| 4 – 8 | Moderate |
| >8 | Strong |

When tested by the above procedure, said compounds of formulas I, II, IV and V as noted above were found to have R values >2, the more active and preferred compounds having R values >8 and >10.

The more active and preferred compounds are further evaluated at multiple doses, e.g., 100, 25, 6.2 and 1.6 mg./kg, by the IgE-mediated PCA in rats. The test procedure for each dose is the same as given above, except for the interpretation of results. If two or more doses of a compound have response lines (diameter vs. antibody dilution) that are parallel to each other and to controls, the potency of such a compound is expressed by $d(Ab)_3$, that is, the dose of a drug that would necessitate tripling of the concentration of antibody for the control rats in order to achieve the same response line as for the medicated rats. The $d(Ab)_3$ value is calculated as follows: The "R" values are plotted vs. the doses in mg./kg. on a log-log graph. A best fitting line is drawn through the points, and a dose in mg./kg. corresponding to R=3 is read as the $d(Ab)_3$. The hereinabove-noted preferred embodiments, when tested by said procedure, were found to have $d(Ab)_3$ values ranging from about 2 to 16, the lower the value the more active the compound.

The actual determination of the numerical antiallergic data definitive for a particular compound of the invention is readily obtained according to the above-described standard test procedures by technicians versed in pharmacological test procedures, without any need for any extensive experimentation.

The compounds of the invention can be prepared for use by dissolving under sterile conditions a salt form of the compounds in water (or an equivalent amount of a nontoxic acid if the free base is used), or in a physiologically compatible aqueous medium such as saline, and stored in ampules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like. Also, the compounds can be formulated for oral administration in aqueous alcohol, glycol or oil solutions or oil-water emulsions in the same manner as conventional medicinal substances are prepared.

We claim:

1. A compound of the formula

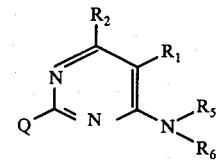

where Q is 4- or 3- or 2-pyridinyl or 4- or 3- or 2-pyridinyl having one or two lower-alkyl substituents or N-oxide thereof, $R_1$ is hydrogen, lower-alkyl or cyano, $R_2$ is hydrogen, loweralkyl, hydroxy or halo, $R_5$ is hydrogen, lower-alkyl or lower-hydroxyalkyl and $R_6$ is lower-alkyl or lower-hydroxyalkyl.

* * * * *

UNITED STATES PATENT AND TRADEMARK OFFICE
CERTIFICATE OF CORRECTION

PATENT NO. : 4,086,233
DATED : April 25, 1978
INVENTOR(S) : George Y. Lesher and Baldev Singh It is certified that error appears in the above-identified patent and that said Letters Patent are hereby corrected as shown below:

Column 2, line 33, "of" should read -- or --.

Column 20, Claim 1, line 33, "loweralkyl" should read -- lower-alkyl --.

Signed and Sealed this

Tenth Day of October 1978

[SEAL]

Attest:

RUTH C. MASON
Attesting Officer

DONALD W. BANNER
Commissioner of Patents and Trademarks